(12) United States Patent
Hill et al.

(10) Patent No.: US 6,746,412 B1
(45) Date of Patent: Jun. 8, 2004

(54) DEVICE FOR MANIPULATING A STYLET UNIT

(75) Inventors: Rolf Hill, Järfälla (SE); Göran Johansson, Södertälje (SE); Maria Wargelius, Stockholm (SE); Per Jarl, Järfälla (SE)

(73) Assignee: St. Jude Medical AB, Järfälla (SE)

( * ) Notice: Subject to any disclaimer, the term of this patent is extended or adjusted under 35 U.S.C. 154(b) by 264 days.

(21) Appl. No.: 10/088,782
(22) PCT Filed: Sep. 19, 2000
(86) PCT No.: PCT/SE00/01816
§ 371 (c)(1), (2), (4) Date: Mar. 22, 2002
(87) PCT Pub. No.: WO01/21243
PCT Pub. Date: Mar. 29, 2001

(30) Foreign Application Priority Data

Sep. 22, 1999 (SE) ............................. 9903430

(51) Int. Cl.$^7$ .................................. A61B 5/00
(52) U.S. Cl. .................................... 600/585
(58) Field of Search ................ 600/373, 585; 606/129; 226/127; 81/487

(56) References Cited

U.S. PATENT DOCUMENTS

| | | | |
|---|---|---|---|
| 4,858,810 A | | 8/1989 | Intlekofer et al. |
| 5,170,787 A | | 12/1992 | Lindegren |
| 5,275,151 A | * | 1/1994 | Shockey et al. ............ 600/585 |
| 5,364,352 A | * | 11/1994 | Cimino et al. ........... 604/95.04 |
| 5,409,453 A | * | 4/1995 | Lundquist et al. ............ 604/22 |
| 5,666,970 A | * | 9/1997 | Smith ........................ 600/585 |
| 5,752,915 A | * | 5/1998 | Neubauer et al. ........... 600/585 |

FOREIGN PATENT DOCUMENTS

| EP | 0 534 747 | 9/1992 |
|---|---|---|
| WO | WO 99/12600 | 3/1999 |

OTHER PUBLICATIONS

846 Research Disclosure, Jul. 1998, Publication 41106.

* cited by examiner

Primary Examiner—Max F. Hindenburg
Assistant Examiner—David J. McCrosky
(74) Attorney, Agent, or Firm—Schiff Hardin LLP

(57) ABSTRACT

A device for manipulating a stylet unit for positioning a electrode cable in a body cavity has a handle supporting, at a distal portion thereof, a rotatable bracket member. A slide member carrying a screw for fixation of a proximal contact element of the electrode cable is displaceably mounted on the bracket member so as to be adjustable to variations in length of a central lumen of the electrode cable, into which the stylet unit is to be inserted.

10 Claims, 2 Drawing Sheets

DEVICE FOR MANIPULATING A STYLET UNIT

BACKGROUND OF THE INVENTION

1. Field of the Invention

The present invention relates in general to a device for manipulating a stylet for positioning an electrode cable in a body cavity, such as a human heart. More particularly, the present invention relates to a device for manipulating a stylet unit of the type having a stylet sleeve and a guide wire located within the sleeve. The distal end portion of the inner guide wire is pre-shaped into a curved configuration so that when it is freely exposed from the distal end portion of the associated flexible, but stiffer stylet sleeve by performing a relative displacement between the latter and the guide wire, the free distal end portion of the guide wire will be capable of bending the distal end portion of the electrode cable into a desired curved shape. In this manner, the tip of the electrode cable may be bent between a substantially straight configuration to a substantially J-shaped configuration in order to locate and fixate the tip of the electrode cable at a suitable site in the heart.

2. Description of the Prior Art

U.S. Pat. No. 5,170,787 discloses a device for manipulating a stylet unit of the kind referred to above for in vivo positioning of an electrode cable. This known device has a handle having a first handle member and a second handle member attached to one another for mutual movements thereof, one of the handle members being connected to a proximal end portion of one of the stylet sleeve and guide wire, the other of said handle members being connected to a proximal end portion of the other of the stylet sleeve and guide wire. This device further has means attached to a distal end portion of one of the first and second handle members for fixation of a proximal contact element of the electrode cable to that one of the first and second handle members. Such a prior art device normally operates smoothly and flawlessly with electrode cables having substantially the same length of the central lumen into which the stylet unit is to be inserted. Thus, in order to obtain proper function of the device, e.g. to ensure accurate control of the electrode tip while positioning the same in e.g. a heart, it is important that the distal tip of the guide wire always reaches the bottom end of the lumen, while the proximal contact element of the electrode cable is fixated to its associated handle member of the device. Although the overall outer length of the electrode cables may be substantially identical, the length of their inner central lumen may vary in dependence of the actual electrode tip design being used, e.g. active (screw-in) or passive fixation (fins or tines). Also manufacturing tolerances of some models of the electrode cables may vary within the range ±1.3 cm. In the preferred embodiment of the stylet manipulating device of U.S. Pat. No. 5,170,787, the distance between the distal end of the guide wire and the point of fixation of the proximal element of the electrode cable to the associated one of the handle members should be a fixed distance, i.e. the associated handle member should be a stationary handle member to which the guide wire is attached, and the other handle member should be a displaceable handle member to which the stylet sleeve is attached. Such a known fixed length-manipulating device therefore is not suitable for accurate handling of the tip of the electrode cables having various lengths of the lumen thereof.

In order to modify existing stylet manipulating devices of the above-mentioned type so as to accommodate lumen length variations and manufacturing tolerances, it has been suggested (see "846/Research Disclosure. July 1998, publication 41106") to provide a set of adapters of various lengths (FIGS. 2 and 3) which are detachably mountable to one and the same handle unit. These adapters are made to fit various predetermined electrode lumen lengths. Furthermore, FIG. 4 of this publication "41106" indicates the use of a telescopic adapter assembly to accommodate lumen length variations by means of one single handle/stylet unit. Such a telescopic assembly requires rather complicated and expensive structural means in order to obtain accurate and stable length adjustments and to prevent mutual rotation of the telescopic elements.

SUMMARY OF THE INVENTION

It is an object of the present invention to eliminate the aforementioned short-comings of the prior art devices and to provide a simplified stylet manipulating device, which has one single stylet/handle unit which can be used for manipulations of electrode cables having various lumen lengths.

The above object is achieved in accordance with the principles of the present invention in a device for manipulating a stylet unit wherein the stylet unit has a stylet sleeve and a guide wire located in the sleeve, the device having a handle with a first handle member and a second handle member attached to each other for movement relative to each other, one of said handle members being connected to a proximal end of one of the stylet sleeve and guide wire, and the other of the handle members being connected to a proximal end of the other of the stylet sleeve and guide wire, a fixation arrangement attached to a distal end of one of the first and second handle members for fixing a proximal contact element of the electrode cable to the handle member to which it is attached, the fixation arrangement being displaceably mounted relative to the handle member to which it is attached so as to be adjustable to accommodate variations in length of a central elongated lumen of the electrode cable into which the stylet unit is to be inserted, and wherein the fixation arrangement has a slide member slidably mounted in a single bracket member having a proximal base portion rotatably attached to the handle member to which the fixation element is attached, and a distal shaft portion with a guide track for the slide member, the slide member carrying a locking mechanism for securing the proximal contact element of the electrode cable to the slide member.

DESCRIPTION OF THE PREFERRED EMBODIMENTS

Figure 1:
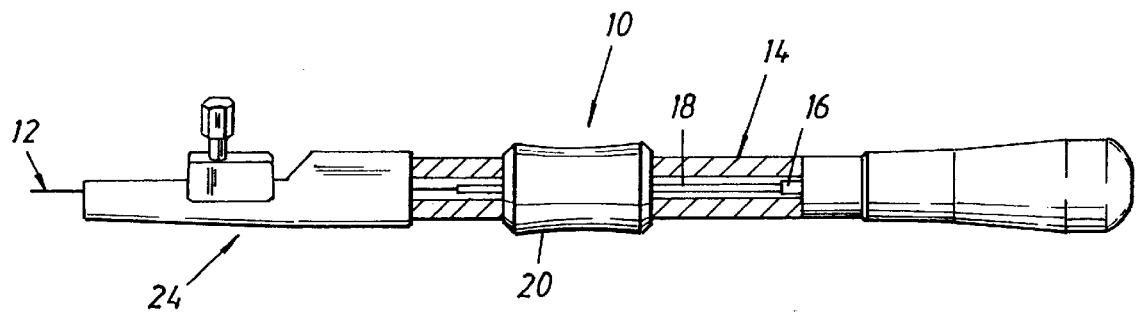
FIG. 1 is a side view of a first embodiment of a stylet manipulating device of the present invention.

FIG. 1 illustrates a device 10 of the present invention for manipulating a stylet unit 12 consisting of a tubular stylet sleeve and a guide wire located within the sleeve, for positioning of an electrode cable in a body cavity, such as a heart. The device 10 has a handle 14 to be hand-held by an operator during implantation of the electrode cable. The proximal or rear end of the guide wire is fixated in the rear part of the handle 14 and extends forwardly through a first stationary guide tube 16 and through a second guide tube 18 which is attached to a stylet sleeve maneuvering element 20 and telescopically slidable within the first guide tube 16 when the maneuvering element 20 is pushed back and forth by the thumb and the index finger of the operator. The proximal or rear end of the stylet sleeve is secured to the inside of the second guide tube 16 for movement together therewith. The stylet unit 12, i.e. the stylet sleeve and the guide wire, extends further forwardly through a central passage 22 in a bracket member 24 which is rotatably attached to the distal end portion of the handle 14, and through a passage 26 in a slide member 28 for fixation of a proximal contact element of the electrode cable to be connected to the manipulating device 10.

In a free state, i.e. when the stylet sleeve is retracted rearwardly, the distal end portion (not shown) of the guide wire of the stylet unit 12 has a pre-shaped curved configuration so as to be able to—in a known manner—bend the distal end of the electrode cable into a desired curved configuration, such as a J-shape, when the stylet unit 12 is fully inserted to the bottom of the central lumen of the electrode cable.

Figure 2:
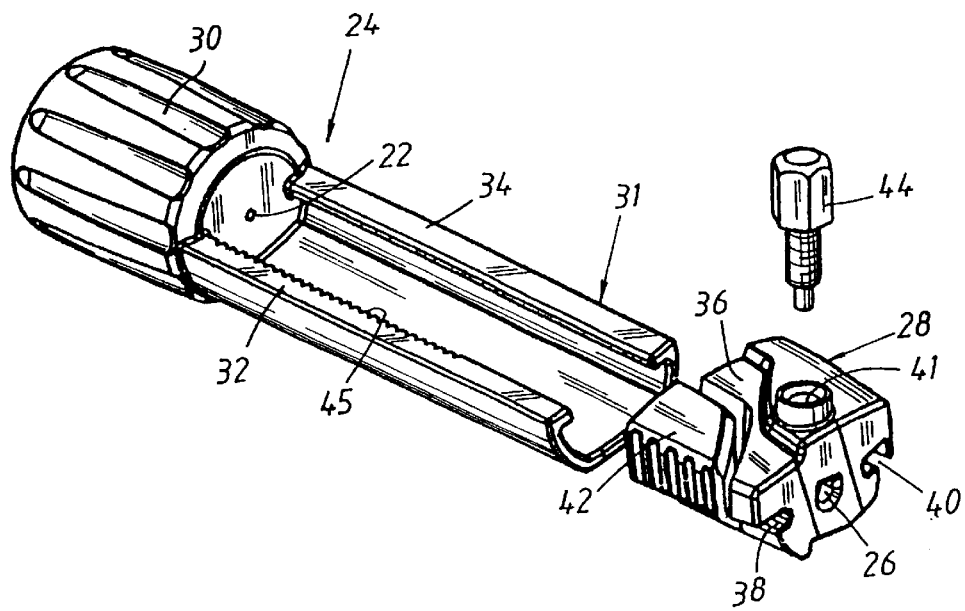
FIG. 2 is an exploded perspective view of a bracket and a slidable fixation means of the device in FIG. 1.
Figure 3:
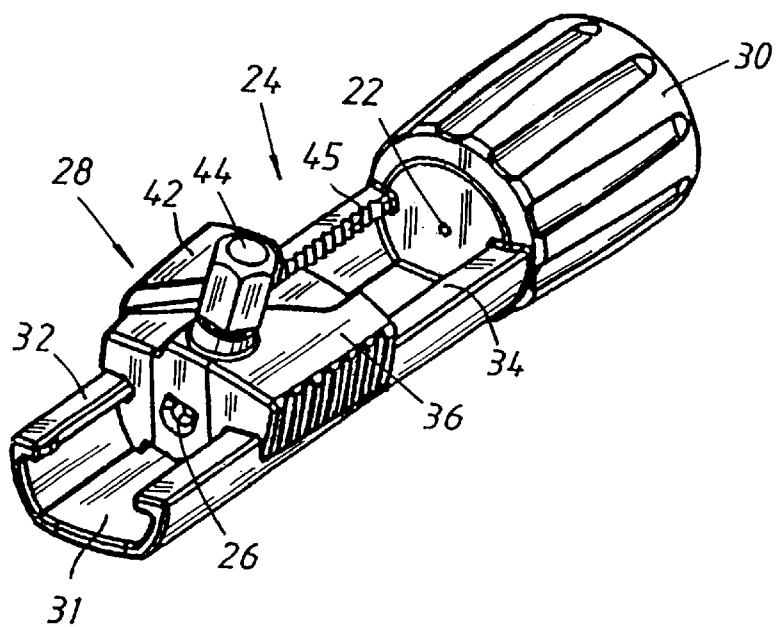
FIG. 3 is a perspective view of the bracket and the slidable fixation means in FIG. 2 in the assembled state.

In order to adapt the manipulating device 10 to different electrode cables respectively having different lengths of the central lumen, i.e. to make it possible to adjust the longitudinal position of the fixation of the proximal contact element of the electrode cable to the handle 14, while holding the distal end of the guide wire against the bottom of the electrode lumen, the fixation slide member 28 is longitudinally slidable in the bracket member 24 and securable in a desired position therein. As shown in FIGS. 1–3, in the preferred embodiment of the invention the bracket member 24 has a proximal base portion 30 which is rotatably attached to the distal end of the handle 14, and a distal shaft portion 31 having a substantially U-shaped cross-section with parallel and inwardly directed flanges 32–34 for guidance of the fixation slide member 28 along the shaft portion 31. The slide member 28 has a body portion 36 has opposite side walls on which guide tracks or grooves 38,40, are respectively formed, that are complementary with the flanges 32,34, respectively, on the shaft portion 31. A threaded bore 41, extending from a top wall of the body portion 36 into the passage 26, is adapted to receive a screw 44 for fixation of the proximal contact element of the electrode cable to the slide member 28. The slide member 28 in its turn is lockable to the shall portion 31 by a locking knob 42 formed integrally with the body portion 36 and spring-biased transversely towards the flange 32 such that one or more lugs (not shown) on the knob 42 may be brought into locking engagement with a toothed rim 45 on the flange 32 at a desired position along the shaft portion 31. The slide member 28 may be released from its locked position by pressing the knob 42 towards the body portion 36.

Instead of having interlocking lugs and teeth, the slide member 28 may be held in a suitable position on the bracket member 24 by frictional engagement between these components, or by a separate lock screw (not shown) clamping the slide member to the shaft portion.

Figure 4:
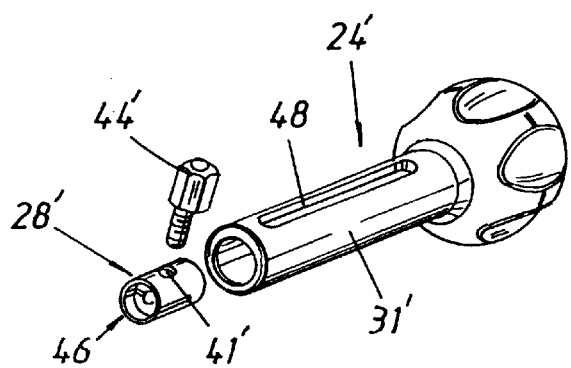
FIG. 4 is an exploded perspective view of an alternative embodiment of a bracket and a slide assembly of a stylet-manipulating device of the present invention.

A second embodiment of the bracket and slide member assembly of the manipulating device of the present invention is shown in FIG. 4. In contrast to the first embodiment in FIGS. 1–3, the shaft portion 31' of the bracket member 24' has a tubular shape, and a cylindrical slide member 28' fits slidably in the tubular shaft portion 31'. The slide member 28' has a central passage for the penetration of the stylet unit 12, and a widened distal orifice 46 for receiving the proximal contact element of the electrode cable. A screw 44' is adapted to extend radially through an elongate axial slot 48 in the shaft portion 31' and into engagement with a threaded bore 41' in the cylindrical slide member 28' such that the screw 44' is capable of fixating the proximal contact element of an electrode cable in the orifice 46 as well as locking the slide member 28' in a desired position in the shaft portion 31' by expanding flexible parts of the slide member 28' by further tightening of the screw 44'.

Although modifications and changes may be suggested by those skilled in the art, it is the intention of the inventors to embody within the patent warranted hereon all changes and modifications as reasonably and properly come within the scope of their contribution to the art.

What is claimed is:

1. A device for manipulating a stylet unit having a stylet sleeve and a stylet guide wire disposed within the stylet sleeve, for positioning an electrode cable in a body cavity, said electrode cable having a central elongated lumen into which the stylet unit is to be inserted, said device comprising:

a handle having a first handle member and a second handle member attached to each another for relative movements thereof, said handle members respectively being connected to respective proximal ends of said stylet sleeve and said stylet guide wire;

a fixation arrangement attached to a distal portion of one of said handle members adapted for fixing a proximal contact element of the said electrode cable to said one of the said handle members, said fixation arrangement being displaceably mounted relative to said one of said handle members so as to be adjustable to accommodate variations in length of said central elongated lumen of said electrode cable; and said fixation arrangement comprising a slide member slidably mounted in a single bracket member having a proximal base portion rotatably attached to said one of said handle members, and a distal shaft portion having a guide track for said slide member, said slide member carrying a locking mechanism adapted for securing said proximal contact element of said electrode cable to said slide member.

2. A device as claimed in claim 1 wherein said shaft portion of said bracket member has a substantially U-shaped cross-section with inwardly directed flanges.

3. A device as claimed in claim 2 wherein said slide member has grooves that are complementary with said flanges of said bracket shaft portion.

4. A device as claimed in claim 2 wherein said locking mechanism locks said slide member to said bracket member by frictional engagement between said slide member and said bracket member.

5. A device as claimed in claim 4 wherein said slide member has flexible portions which exert transversely directed biasing forces on said bracket shaft portion.

6. A device as claimed in claim 5 wherein one of said flexible portions has at least one locking protrusion thereon engageable with ratchet teeth on one of said flanges of said distal shaft portion.

7. A device as claimed in claim 2 wherein said locking mechanism locks said slide member to said bracket member by a ratchet mechanism.

8. A device as claimed in claim 7 wherein said slide member has flexible portions which exert transversely directed biasing forces on said bracket shaft portion.

9. A device as claimed in claim 8 wherein one of said flexible portions has at least one locking protrusion thereon engageable with ratchet teeth on one of said flanges of said distal shaft portion.

10. A device as claimed in claim 1 wherein said shaft portion of said bracket member is tubular and has a longitudinal slot for receiving said locking mechanism, said locking mechanism being slidable within said tubular shaft portion.

* * * * *